United States Patent [19]
Homra

[11] Patent Number: 5,927,974
[45] Date of Patent: Jul. 27, 1999

[54] HOLDER FOR ORAL SUCTION DEVICE

[76] Inventor: Ronald A. Homra, 65 Stonewall Dr., Jackson, Tenn. 38305

[21] Appl. No.: 09/020,865

[22] Filed: Feb. 9, 1998

Related U.S. Application Data

[63] Continuation-in-part of application No. 08/865,214, May 29, 1997.

[51] Int. Cl.[6] .................................................. A61G 15/00
[52] U.S. Cl. ............................................................ 433/77
[58] Field of Search .................................. 433/77, 78, 91, 433/116; 312/209; 604/263

[56] References Cited

U.S. PATENT DOCUMENTS

| | | |
|---|---|---|
| 2,214,775 | 9/1940 | Pieper ......................................... 433/78 |
| 3,198,574 | 8/1965 | Ota et al. .................................... 433/78 |
| 3,802,736 | 4/1974 | Valeska ....................................... 433/78 |
| 4,648,839 | 3/1987 | Timerdahl et al. ........................ 433/77 |
| 5,161,970 | 11/1992 | Baskas ......................................... 433/77 |
| 5,406,939 | 4/1995 | Bala .......................................... 206/438 |

*Primary Examiner*—John J. Wilson
*Attorney, Agent, or Firm*—Walker, McKenzie & Walker, P.C.

[57] ABSTRACT

A holder for use with a support member and an oral suction device having a distal end for suctioning a patient's oral cavity. The holder includes a sleeve having an interior and an entrance opening communicating with the interior; and a mount for mounting the sleeve to the support member so that the distal end of the oral suction device can be inserted into the sleeve after the sleeve is mounted to the support member.

10 Claims, 7 Drawing Sheets

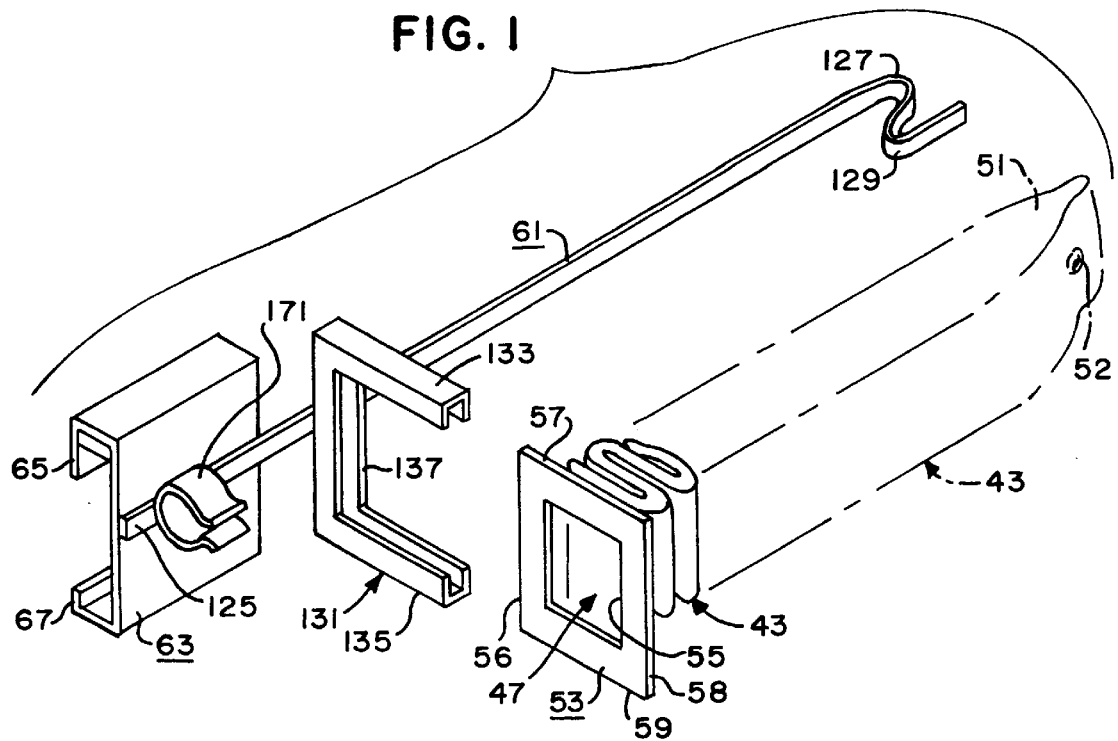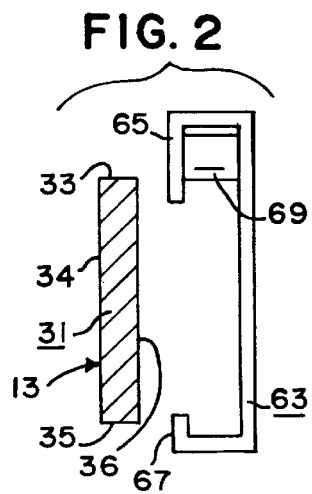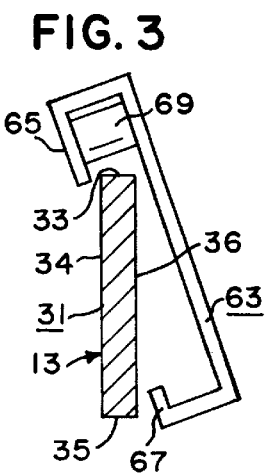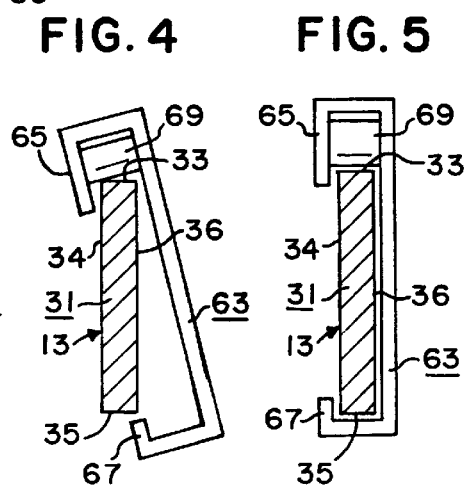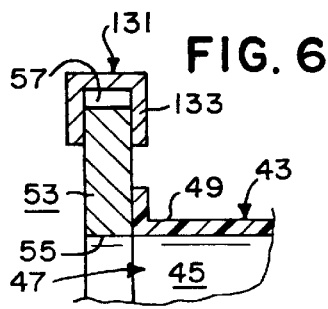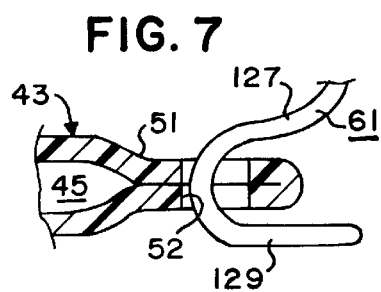

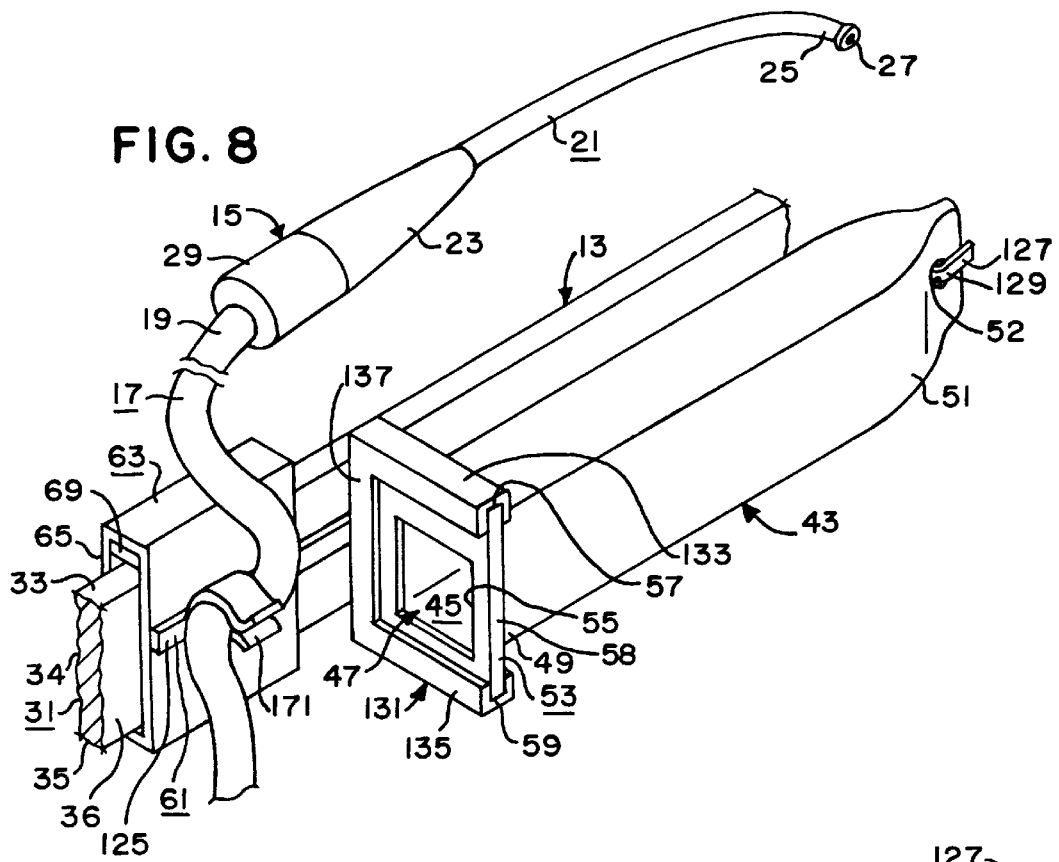
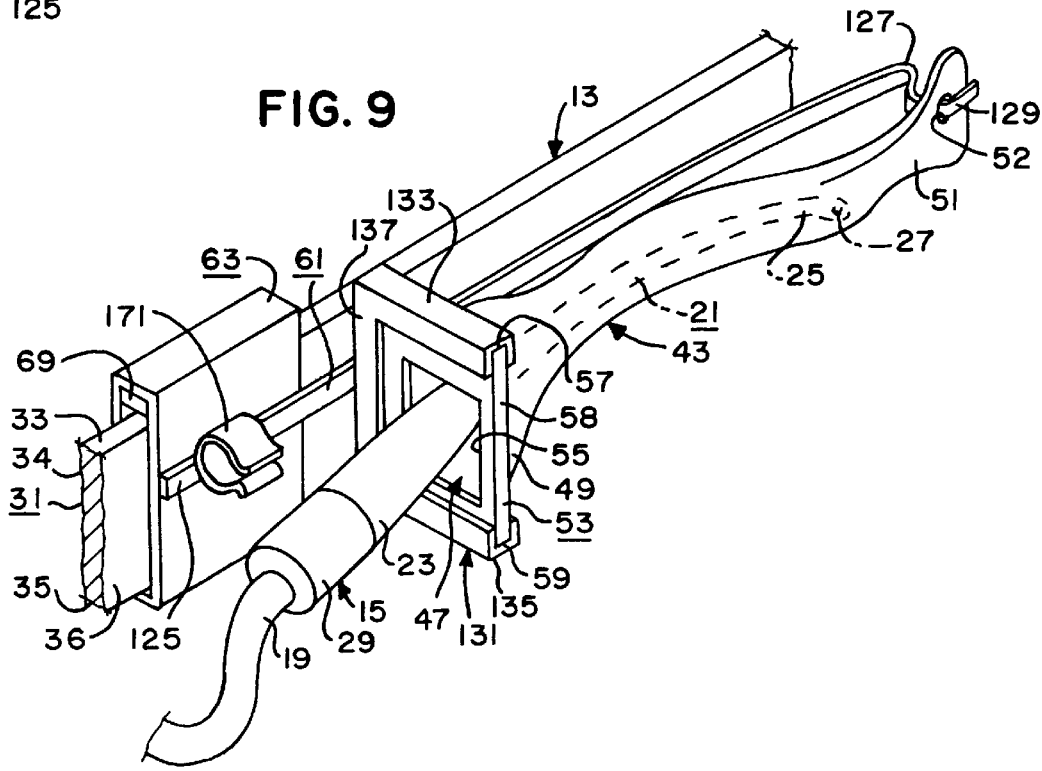

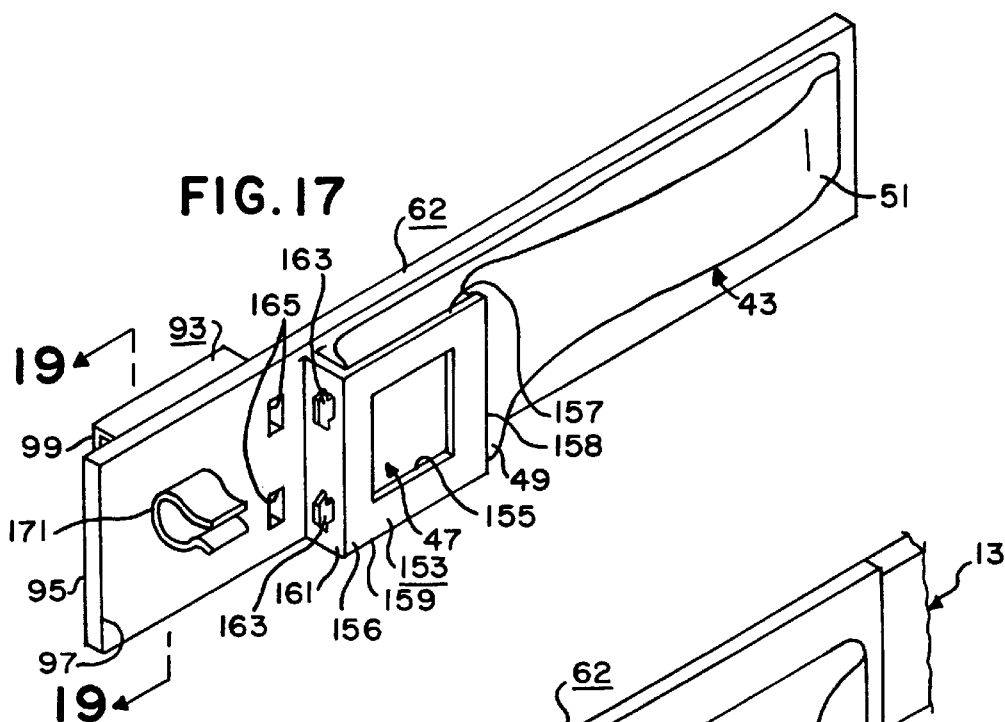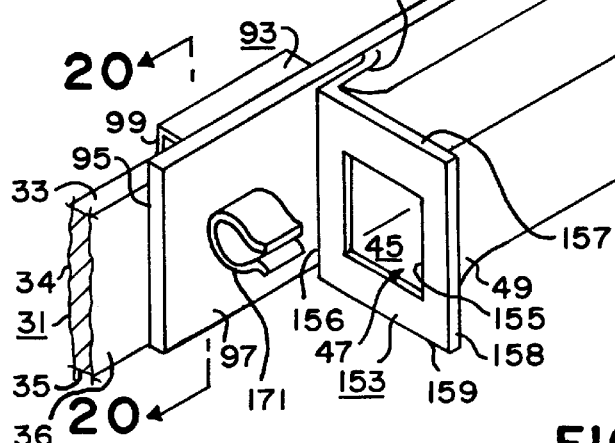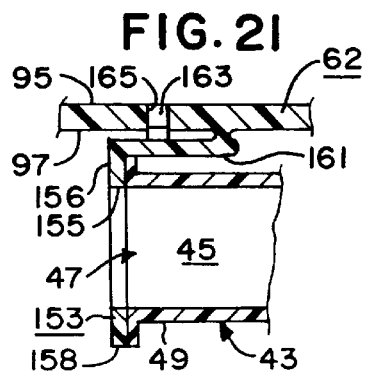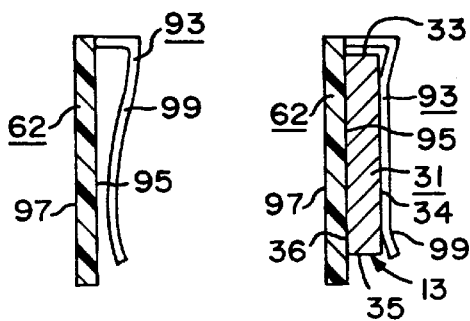

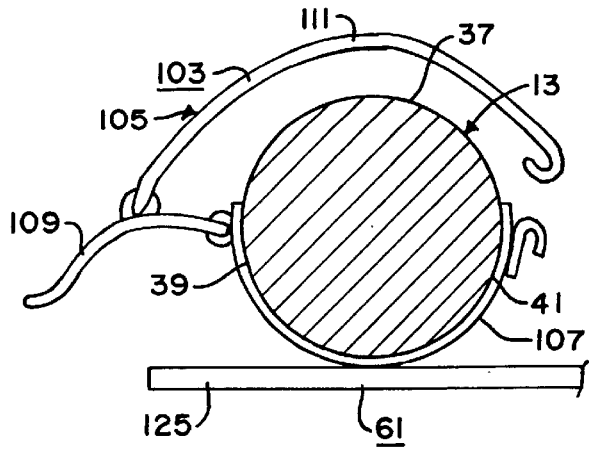
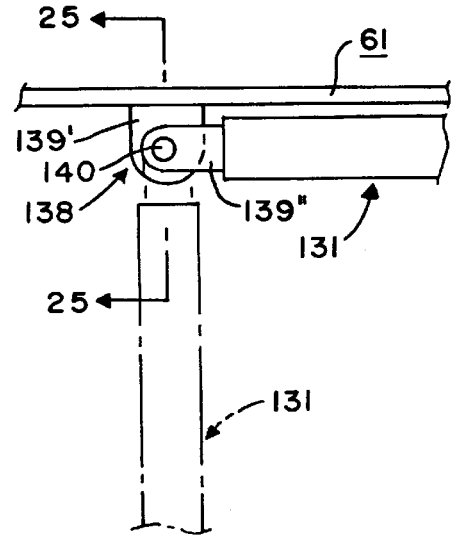
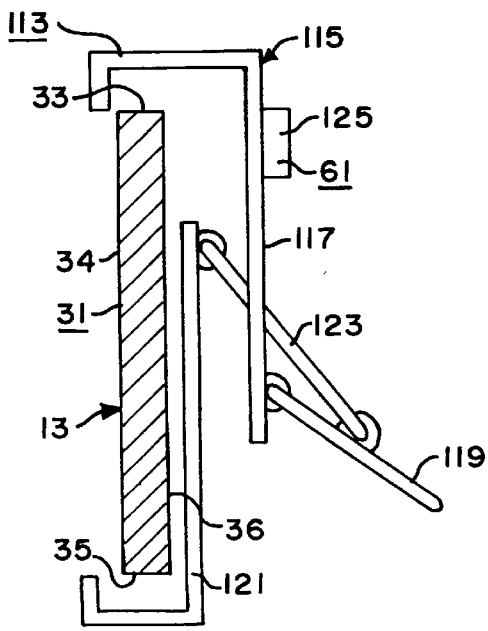
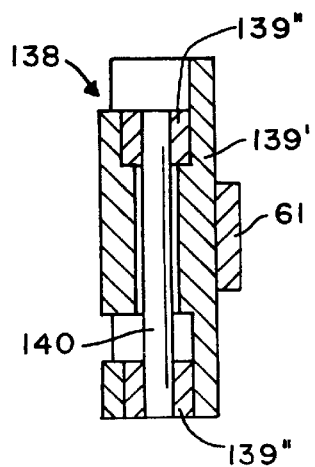

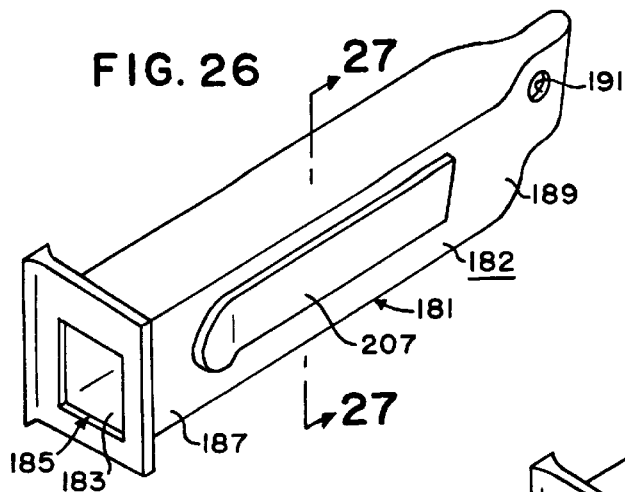
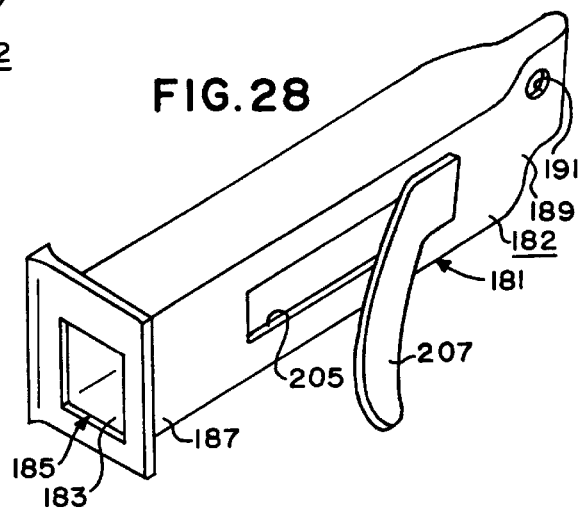
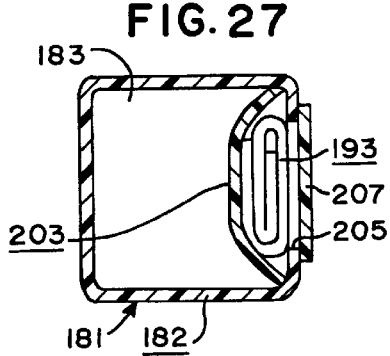
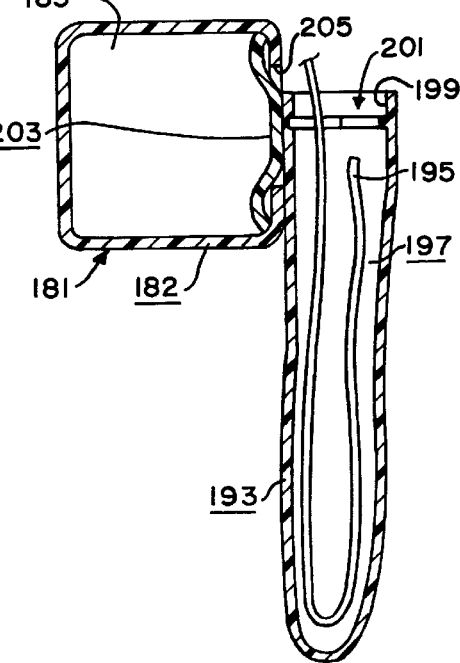
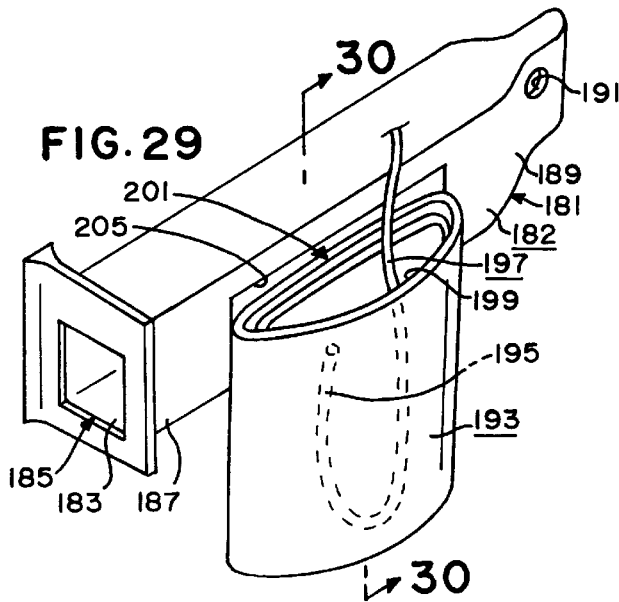

HOLDER FOR ORAL SUCTION DEVICE

CROSS-REFERENCE TO RELATED APPLICATIONS

This is a continuation-in-part of application Ser. No. 08/865,214, entitled "HOLDER FOR ORAL SUCTION DEVICE," filed May 29, 1997, now pending. Such specifically enumerated prior application is hereby incorporated herein by reference.

STATEMENT RE FEDERALLY SPONSORED RESEARCH OR DEVELOPMENT

Not Applicable.

REFERENCE TO A "MICROFICHE APPENDIX"

Not Applicable.

BACKGROUND OF THE INVENTION

1. Field of the Invention

The present invention relates, in general, to means for holding an oral suction device during an operation and the like.

2. Information Disclosure Statement

Oral suction devices are commonly used by anesthesiologists and other health care professionals for suctioning fluid, etc., from patient's mouths during operations, while the patient is in intensive care, etc. Such oral suction devices commonly include an elongated, flexible hose having a proximal end for being attached to a vacuum source and a distal end, and a relative rigid suction tube having a proximal end for being attached to the distal end of the hose and a distal end with one or more apertures therein for being inserted into a patient's mouth to suction the oral cavity during surgery, etc. The proximal end of the suction tube preferably has a handle portion provided thereon or formed integrally therewith to allow an anesthesiologist or other health care professional to easily and accurately manipulate the suction tube. Such suction tubes are provided in sterile packages for use during a single operation, etc., and are sold by Sherwood Medical of St. Louis, Mo. 83103, as ARGYLE™ Yankauer Suction Tubes.

A serious problem with the use of such suction tubes is what to do with the tube after its initial use. That is, after a suction tube is first used to suction a patient's mouth, it's exterior surfaces will be covered with body fluid and/or blood, etc., from the patient's mouth. Even if the suction tube is the disposable type, it is generally meant to be used throughout a single operation or procedure. Under current practice, it is typical for an anesthesiologist to initially use a suction tube to suction a patient's mouth and then remove the tube from the patient's mouth and lay the suction tube down on any convenient surface for later use during the same operation. Because of the lack of convenient surfaces, it is common for an anesthesiologist to merely lay the suction tube on the operating bed, or insert the suction tube beneath the edge of the mattress of the operating bed, etc. Such practices can result contamination of the suction tube, the operating bed, and/or operating room personnel, etc.

A preliminary patentability search conducted in class 433, subclasses 91, 97, 60, 77 and 79, and class 604, subclasses 35, 54, 195, 192, 163, 199, 261 and 262, produced the following patents which appear to be relevant to the present invention:

Baskas, U.S. Pat. No. 5,161,970, issued Nov. 10, 1992, discloses a tool holder for mounting on the instrument panel in a dentist's office. The tool holder has a grooved surface for receiving one or more holders for syringes, scalpels, etc. These holders have hexagonal bases for mounting in one of several different positions.

Bala, U.S. Pat. No. 5,406,939, issued Apr. 18, 1995, discloses a protective sheath for an endoscope probe comprising first and second elongated plastic sheets peripherally sealed together at the sides and distal ends thereof, while being unsealed at the proximal ends. The first sheet is transparent and has greater optical clarity than the second sheet, while the second sheet has better frictional slip characteristics than the first sheet.

Nothing in the known prior art discloses or suggests the present invention. More specifically, nothing in the known prior art discloses or suggests an oral suction device holder including a sleeve having an interior and an entrance opening communicating with the interior; and a mount for mounting the sleeve to a support member so that the distal end of the oral suction device can be inserted into the sleeve after the sleeve is mounted to the support member.

BRIEF SUMMARY OF THE INVENTION

The present invention provides a device for holding the distal end of an oral suction device. A basic concept of the present invention is to provide a device that can be mounted to an operating bed or IV pole for holding the distal end of a oral suction device.

The oral suction device holder of the present invention comprises, in general, a sleeve having an interior and an entrance opening communicating with the interior; and a mount for mounting the sleeve to a support member so that the distal end of the oral suction device can be inserted into the sleeve after the sleeve is mounted to the support member.

One object of the present invention is to provide an oral suction device holder which prevents contamination and the spread of viral and bacterial diseases after suctioning the oral cavity while the patient is in the operating room, etc.

Another object of the present invention is to provide such a device which protects hospital personnel, etc., especially anesthesia personnel, from oral secretions.

Another object of the present invention is to provide such a device specifically designed to integrate into the operating room environment when used to suction the oral cavity during surgery.

BRIEF DESCRIPTION OF THE SEVERAL VIEWS OF THE DRAWINGS

FIG. 1 is an exploded perspective view of a first embodiment of the oral suction device holder of the present invention.

FIGS. 2, 3, 4 and 5 are somewhat diagrammatic side elevational views of a portion of the oral suction device holder of FIG. 1, showing how the mount of the oral suction device holder of FIG. 1 is attached to the side bar of an operating bed.

FIG. 6 is a somewhat diagrammatic sectional view of a portion of the oral suction device holder of FIG. 1, showing a portion of a sleeve of the oral suction device holder of FIG. 1 attached to a portion of a frame and frame track thereof.

FIG. 7 is a somewhat diagrammatic sectional view of a portion of the oral suction device holder of FIG. 1, showing the distal end of the sleeve of the oral suction device holder of FIG. 1 attached to a body thereof.

FIG. 8 is a perspective view of the oral suction device holder of FIG. 1, shown in combination with the side bar of an operating bed and an oral suction device.

FIG. 9 is a perspective view similar to FIG. 8, but showing the distal end of the suction tube of the oral suction device inserted into the sleeve of the oral suction device holder of FIG. 1.

FIG. 16 is a top plan view of a portion of the embodiment of FIG. 15, shown combined with a standard IV pole or the like.

FIG. 17 is a perspective view of an alternate embodiment of a portion of the oral suction device holder of the present invention, shown in a closed position.

FIG. 18 is a perspective view of the oral suction device holder of FIG. 17, shown in an opened position and in combination with the side bar of an operating bed.

FIG. 19 is a sectional view substantially as taken on line 19—19 of FIG. 17, with portions omitted for clarity.

FIG. 20 is a sectional view substantially as taken on line 20—20 of FIG. 18, with portions omitted for clarity.

FIG. 21 is a sectional view substantially as taken on line 21—21 of FIG. 18, with portions omitted or broken away for clarity.

FIG. 22 is a somewhat diagrammatic view of an alternate clamp of the oral suction device holder of the present invention, shown in combination with a typical IV pole or the like.

FIG. 23 is a somewhat diagrammatic view of another alternate clamp of the oral suction device holder of the present invention, shown in combination with the side bar of an operating bed.

FIG. 24 is a somewhat diagrammatic top plan view of a portion of the oral suction device holder of FIG. 1, showing a modified attachment between the body member and the frame track thereof which allows the frame track to move between a first or in-use position as shown in broken lines in FIG. 24 and a second or stored position as shown in solid lines in FIG. 24.

FIG. 25 is a sectional view substantially as taken on line 25—25 of FIG. 24 with portions thereof omitted for clarity and on a somewhat enlarged scale.

FIG. 26 is perspective view of a second embodiment of the sleeve of the oral suction device holder the present invention.

FIG. 27 is a sectional view substantially as taken on line 27—27 of FIG. 26 on a somewhat enlarged scale.

FIG. 28 is a perspective view similar to FIG. 26 but showing a tear strip thereof partially torn off to reveal an internal pocket of the sleeve.

FIG. 29 is a perspective view similar to FIGS. 26 and 28 but showing the tear strip completely torn off and an external pouch or bag extending from the internal pocket of the sleeve.

FIG. 30 is a sectional view substantially as taken on line 30—30 of FIG. 29 on a somewhat enlarged scale.

DETAILED DESCRIPTION OF THE INVENTION

Figure 10:
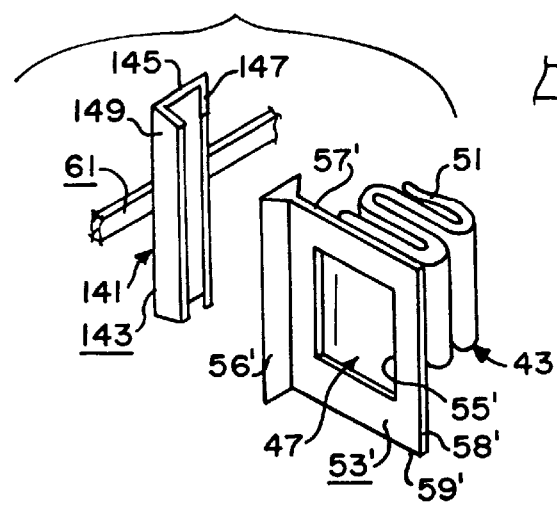
FIG. 10 is an exploded perspective view of an alternate embodiment of a portion of the oral suction device holder of the present invention.

The holder of the present invention is especially designed for use with a support member 13 and an oral suction device 15 such as commonly used by anesthesiologists and other health care professionals for suctioning fluid, etc., from patient's oral cavities during operations, while the patient is in intensive care, etc.

As illustrated in FIGS. 8 and 9, a typical oral suction device 15 commonly includes an elongated, flexible hose 17 having a proximal end (not shown) for being attached to a vacuum source (not shown) and a distal end 19, and a relative rigid suction tube 21 having a proximal end 23 for being attached to the distal end 19 of the hose 17, and a distal end 25 with one or more apertures 27 therein for being inserted into a patient's oral cavity or mouth to suction the patient's oral cavity during surgery, etc. A grip portion or handle 29 is preferably provided at or adjacent, or formed integrally with the proximal end 23 of the suction tube 21 to allow an anesthesiologist or other health care professional to easily and accurately manipulate the suction tube 21. Such suction tubes are provided in sterile packages for use during a single operation, etc., and are sold by Sherwood Medical of St. Louis, Mo. 83103, as ARGYLE™ Yankauer Suction Tubes.

The support member 13 may consist of an elongated support bar 31 (see FIGS. 2–5, 8, 9, 12–14, 18, 20 and 23) that extends along at least a portion of the head of one side of a typical operating bed or the like. A typical support bar 31 is constructed out of a strong, rigid material such as metal, and may have a substantially rectangular cross-sectional area or shape as clearly shown in, for example, FIGS. 2–5. The cross-sectional dimensions of such a typical support bar 31 may be approximately ⅜ inch (0.95 centimeter) wide, and approximately 1⅛ inches (2.86 centimeters) tall. The support bar 31 preferably has a first or upper edge 33 and a second or lower edge 35.

Alternatively, the support member 13 may consist of an elongated pole 37 (see FIGS. 15, 16 and 22) that extends upward from a support surface such as the floor. The pole 37 has a first side 39 and a second side 41, and may consist of a typical I-V pole of any well known construction. The pole 37 is preferably constructed out of a strong, rigid material such as metal, and may have a substantially circular cross-sectional area or shape as clearly shown in FIGS. 15, 16 and 22. The cross-sectional dimensions of such the pole 37 may be the same as a typical I-V pole, e.g., approximately 0.98 inch (2.5 centimeters) in diameter. The pole 37 preferably extends upward from a support base or the like (not shown) that can be stably supported on the floor or the like.

The oral suction device holder of the present invention includes a sleeve having an interior for receiving the distal end 25 of the suction tube 21, and having an entrance opening communicating with the interior for allowing the distal end 25 of the suction tube 21 to be inserted therethrough.

A first embodiment of the sleeve is shown in FIGS. 1, 6, 7, 8 and 9, and identified by the numeral 43. The sleeve 43 has an interior 45 and a mouth or entrance opening 47 communicating with the interior 45 thereof. The sleeve 43 is preferably elongated and has a first or proximal end 49 adjacent the entrance opening 47, and a second or distal end 51 opposite the entrance opening 47. The second end 51 of the sleeve 43 may have an aperture 52 therethrough for reasons which will hereinafter become apparent. The sleeve 43 is preferably constructed of a material that is flexible, and that is impermeable to viral and bacterial contamination. The sleeve 43 may be made of any impermeable plastic, paper or rubber as an elongated tube-like structure having one opened end and one closed end in any manner now apparent to those skilled in the art such as, for example, by being extruded from a plastic material, etc. Due to the flexible nature of the sleeve 43, the sleeve 43 will typically collapse about the distal end 25 of the suction tube 21 as shown in FIG. 9, when the distal end 25 of the suction tube 21 is inserted into the sleeve 43 and vacuum is supplied to the suction tube 21.

The oral suction device holder of the present invention preferably includes a substantially rigid frame attached to the first end of the sleeve.

A first embodiment of the substantially rigid frame is shown in FIGS. 1, 6, 8 and 9, and identified by the numeral 53. The frame 53 is attached to the sleeve 43 about the entrance opening 47 in the sleeve 43. The frame 53 preferably has an opening 55 therethrough communicating with the entrance opening 47 in the sleeve 43 and the interior 45 of the sleeve 43 to allow the distal end 25 of the suction tube 21 to be inserted through the opening 55 in the frame 53, through the entrance opening 47 in the sleeve 43, and into the interior 45 of the sleeve 43. The frame 53 has a first or inner edge 56, a second or upper edge 57, a third or outer edge 58 and a fourth or lower edge 59. The frame 53 is preferably constructed of a material that is rigid, and that is also impermeable to viral and bacterial contamination. The frame 53 may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc.

Figure 11:
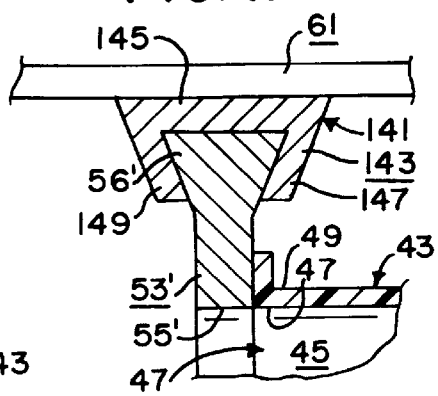
FIG. 11 is a somewhat diagrammatic sectional view of a portion of the oral suction device holder of FIG. 10, showing the frame of the oral suction device holder of FIG. 10 attached to the frame track thereof.

A second embodiment of the substantially rigid frame is shown in FIGS. 10 and 11, and identified by the numeral 53'. The frame 53' is substantially similar to the frame 53 and is attached to a sleeve 43 about the entrance opening 47 in the sleeve 43. The frame 53' preferably has an opening 55' therethrough communicating with the entrance opening 47 in the sleeve 43 and the interior 45 of the sleeve 43 to allow the distal end 25 of the suction tube 21 to be inserted through the opening 55' in the frame 53', through the entrance opening 47 in the sleeve 43, and into the interior 45 of the sleeve 43. The frame 53' has a first or inner edge 56', a second or upper edge 57', a third or outer edge 58' and a fourth or lower edge 59'. However, unlike the inner edge 56 of the frame 53, the inner edge 56' of the frame 53' is flanged-shaped for reasons which will hereinafter become apparent. The frame 53' is preferably constructed of a material that is rigid, and that is also impermeable to viral and bacterial contamination. The frame 53' may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc.

Single or multiple units of the combined sleeve 43 and frame 53 or frame 53' can thus be provided in sterile packages for use by a surgeon, etc.

The oral suction device holder of the present invention includes a mount for mounting a sleeve of the holder to a support member so that the distal end 25 of the suction tube 21 of the oral suction device 15 can be inserted into the sleeve after the sleeve is mounted to the support member. The mount allows a sleeve of the holder to be mounted to the support member 13 so that the distal end 25 of the suction tube 21 of the oral suction device 15 can be easily inserted into and removed from the sleeve after the sleeve is mounted to the support member 13.

The mount preferably includes a body member, and a clamp for clamping the body member to the support member 13.

A first embodiment of the body member is shown in FIGS. 1, 7–10, 15, 16, 22 and 23, and identified by the numeral 61. The body member 61 preferably consist of an elongated, substantially rigid member such as a metal rod or the like as will hereinafter be described in more detail.

A second embodiment of the body member is shown in FIGS. 17–20, and identified by the numeral 62. The body member 62 preferably consists of an elongated, substantially rigid member such as a plastic plate or the like as will hereinafter be described in more detail.

A first embodiment of the clamp is shown in FIGS. 1–5, 8 and 9, and identified by the numeral 63. The clamp 63 is especially designed to be removably attached to the support bar 31. Thus, the clamp 63 preferably includes a first finger 65 for fitting over the first edge 33 of the bar 31, and a second finger 67 for fitting over the second edge 35 of the bar 31 to thereby mount the clamp 63 to the bar 31. The clamp 63 preferably includes spring means 69 for fastening the bar 31 of the support member 13 between the first and second fingers 65, 67 thereof. The spring means 69 may consist merely of a leaf spring or the like mounted within the body of the clamp 63 between the first and second fingers 65, 67 thereof for allowing the clamp 63 to be manually inserted over the bar 31 as shown diagrammatically in FIGS. 2–5 so that the spring means 69 can be compressed as the clamp 63 is inserted over the bar 31 and will expand to secure the bar 31 between the first and second fingers 65, 67 after the clamp 63 is fully inserted over the bar 31 as shown in FIG. 5.

Figure 12:
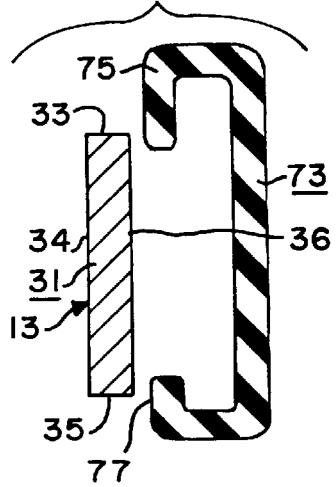
FIGS. 12, 13 and 14 are somewhat diagrammatic sectional views of an alternate embodiment of a portion of the oral suction device holder, showing how the mount of the oral suction device holder thereof is attached to the side bar of an operating bed.
Figure 13:
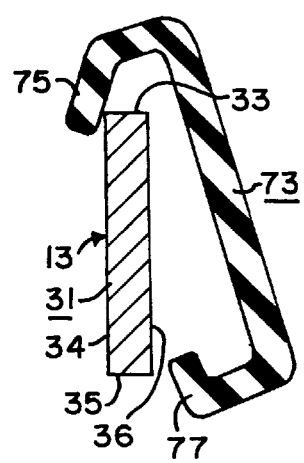
Figure 14:
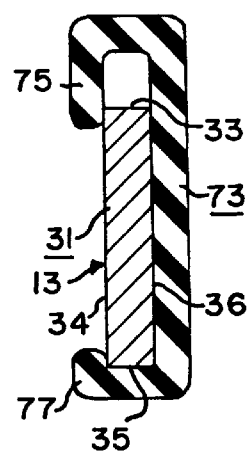

A second embodiment of the clamp is shown in FIGS. 12–14, and identified by the numeral 73. The clamp 73 is also especially designed to be removably attached to the support bar 31. Thus, the clamp 73 preferably includes a first finger 75 for fitting over the first edge 33 of the bar 31, and a second finger 77 for fitting over the second edge 35 of the bar 31 to thereby mount the clamp 73 to the bar 31. At least a portion of the clamp 73 is resilient for allowing the first and second fingers 75, 77 to be spread over the first and second edges 33, 35 of the bar 31 as clearly shown in FIGS. 12–14. Thus, at least the first finger 75, and preferably, the entire body of the clamp 73, is preferably molded or otherwise constructed of a somewhat resilient but substantially rigid plastic or the like so that the body of the clamp 73 can be manually inserted over the bar 31 as shown diagrammatically in FIGS. 12–14 with the first finger 75 being spread away from the second finger 77 somewhat as the clamp 73 is inserted over the bar 31. The first finger 75 will then spring back to its normal position after the clamp 73 is fully inserted over the bar 31 as shown in FIG. 14 to thereby secure the mount to the bar 31 as will now be apparent to those skilled in the art.

Figure 15:
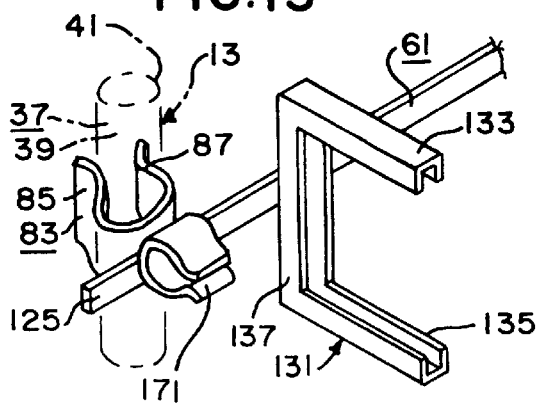
FIG. 15 is a perspective view of an alternate embodiment of a portion of the oral suction device holder of the present invention.
Figure 16:
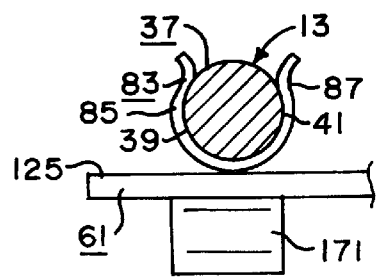

A third embodiment of the clamp is shown in FIGS. 15 and 16, and identified by the numeral 83. The clamp 83 is especially designed to be removably attached to the support pole 37. The clamp 83 preferably consist of a spring member having a first finger 85 for clamping over the first side 39 of the bar 37, and a second finger 87 for clamping over the second side 41 of the pole 37 to thereby mount the clamp 83 to the pole 37. At least a portion of the clamp 83 is resilient for allowing the first and second fingers 85, 87 to be spread over the first and second sides 39, 41 of the pole 37 as clearly shown in FIGS. 15 and 16. Thus, the entire body of the clamp 83 is preferably pressed or otherwise constructed of a somewhat resilient but substantially rigid spring metal or the like so that the clamp 83 can be manually inserted over the pole 37 with the first and second fingers 85, 87 spreading away from one another somewhat as the clamp 83 is inserted over the pole 37, and the springing back toward one another to their normal position after the clamp 83 is fully inserted over the bar 31 as shown in FIG. 16 to thereby secure the mount to the pole 37 as will now be apparent to those skilled in the art.

A fourth embodiment of the clamp is shown in FIGS. 17, 18, 19 and 20, and identified by the numeral 93. The clamp 93 is also especially designed to be removably attached to the support bar 31, and is especially designed for use with the body member 62. The body member 62 preferably includes a substantially flat first or inner face 95, and a substantially flat second or outer face 97. The clamp 93 preferably includes a finger 99 for fitting over the first edge 33 of the bar 31 and for engaging the first face 34 of the bar 31 to springably clamp the bar 31 between the finger 99 and the first face 95 of the body member 62 as clearly shown in FIG. 20. At least a portion of the clamp 93 is resilient for allowing the finger 99 to be spread over the first edge 33 of the bar 31. Thus, at least the finger 99 is preferably molded or otherwise constructed of a somewhat resilient but substantially rigid metal, plastic or the like so that the finger 99 of the clamp 93 can be manually inserted over the bar 31 with the finger 99 being spread away from the first face 95 of the body member 62 somewhat as the clamp 93 is inserted over the bar 31. The finger 99 will then spring back to its normal position after the clamp 93 is fully inserted over the bar 31 as shown in FIG. 20 to thereby clamp the bar 31 between the finger 99 and the first face 95 of the body member 62 as will now be apparent to those skilled in the art.

A fifth embodiment of the clamp is shown in FIG. 22, and identified by the numeral 103. The clamp 103 is also especially designed to be removably attached to the support pole 37. The clamp 103 preferably includes a lever-type clasp 105 for securing to the pole 37. The clasp 105 may include a first member 107 attached to the body member 61 for extending around approximately half of the diameter of the pole 37, a lever 109 pivotally attached to one end of the first member 107, and a second member 111 pivotally attached at one end to a midportion of the lever 109 and hookably attachable at the other end to the end of the first member 107 opposite the lever 109 so that the clasp can be securely clamped about the pole 37 by merely placing the first member 107 around a portion of the pole 37, hooking the distal end of the second member 111 to the distal end of the first member 107, and then closing the lever 109 to draw the first and second members 107, 109 against the pole 37 as will now be apparent to those skilled in the art.

A sixth embodiment of the clamp is shown in FIG. 23, and identified by the numeral 113. The clamp 113 is also especially designed to be removably attached to the support bar 31. Thus, the clamp 113 preferably includes a lever-type clasp 115 for securing to the bar 31. The clasp 115 may include a first member 117 attached to the body member 61, etc., and having a hook-like distal end for hooking over the first edge 33 of the bar 31, a lever 119 pivotally attached to the proximal end of the first member 117, a second member 121 having a hook-like distal end for hooking over the second edge 35 of the bar 31, and a link member 123 pivotally attached at one end to a midportion of the lever 119 and pivotally attached at the other end to the end of the proximal end of the second member 121 so that the clasp can be securely clamped about the bar 31 by merely placing hook-like ends of the first and second members 117, 121 around the opposite edges 33, 35 of the bar 31, and then closing the lever 119 to draw the distal ends of the first and second members 117, 121 against the bar 31 as will now be apparent to those skilled in the art.

As stated hereinabove, the body member 61 preferably consist of an elongated, substantially rigid member such as a metal rod or the like. Thus, the body member 61 includes a first end 125 and a second end 127. The second end 127 of the body member 61 preferably terminates in a hook or hook-like member 129 for allowing the second end 51 of the sleeve 43 to be hooked thereonto. More specifically, the hook 129 is preferably especially designed to extend through the aperture 52 in the second end 51 of the sleeve 43 as clearly shown in FIGS. 7–9 to removably secure the second end 51 of the sleeve 43 to the second end 127 of the body member 61. The clamps 63, 73, 83,103, 113 are preferably rigidly attached to a respective body member 61 adjacent the first end 125 thereof by welding, glue, bolts, etc., as will now be understood by those skilled in the art.

The oral suction device holder of the present invention may include a frame track to for attaching the frame 53 to the mount.

A first embodiment of the frame track is shown in FIGS. 1, 6 8, 9 and 15, and identified by the numeral 131. The frame track 131 preferably includes an upper track member 133 for receiving the upper edge 57 of the frame 53, and a lower track member 135 for receiving the lower edge 59 of the frame 53. In addition, the frame track 131 may include an inner track member 137 for receiving the inner edge 56 of the frame 53. Each track member 133, 135, 137 preferably has a groove therein to allow the respective edges 56, 57, 59 of the frame 53 to be easily slide thereinto as will now be apparent to those skilled in the art. More specifically, each track member 133, 135, 137 may be substantially U-shaped in cross-section. The frame track 131 may be molded, stamped or otherwise manufactured out of a substantially rigid metal or plastic, etc., as welded, glued, bolted or otherwise fixedly attached to the body member 61 a spaced distance from the second end 127 of the body member 61 to allow the sleeve 43 to fully extend when the first end 49 thereof is attached via the frame 53 to the frame track 131 and the second end 51 thereof is attached via the hook 129 to the second end 127 of the body member 61.

A modified attachment between the frame track 131 and the body member 61 is shown in FIGS. 24 and 25. This modified attachment includes a hinge 138 attaching the frame track 131 to the body member 61 in a manner which allows the frame track 131 to pivot between a first or in-use position located substantially perpendicular to the body member 61 as shown in broken lines in FIG. 24 and a second or stored position located substantially parallel to the body member 61 as shown in solid lines in FIG. 24. The hinge 138 may include typical structure, such as a first knuckle 139' attached to the body member 61 by welding or the like, a second knuckle or set of knuckles 139" attached to the frame track 131 by welding or the like, and a pivot rod or axle 140 pivotally joining the first and second knuckles 139', 139" in such a manner to allow the frame track 131 to be moved between the fist and second positions. In addition, the hinge 138 may be modified and/or include structure, such as cut-outs in the knuckles, springs (not shown), etc., for allowing the frame track 131 to be manually locked in the first or second positions and for biasing the frame track 131 to the first or second position, etc., as will now be apparent to those skilled in the art.

A second embodiment of the frame track is shown in FIGS. 10 and 11, and identified by the numeral 141. The frame track 141 preferably includes an inner track member 143 for especially designed to receive the flange-like inner edge 56' of the frame 53'. More specifically, the inner track member 143 preferably includes a back wall 145, a first side wall 147 extending outward from one side edge of the back wall 145, and a second side wall 149 extending outward from the other side edge of the back wall 145, with the side walls 147, 149 angled inward toward one another as they extend from the back wall 145 as clearly shown in FIGS. 10 and 11 to grip the flange-like inner edge 56' of the frame 53' when the flange-like inner edge 56' is slid thereinto as will now be apparent to those skilled in the art. The side walls 147, 149 are preferably springable toward and away from one another so that the flange-like inner edge 56' of the frame 53' can be securely gripped thereby. The frame track 141 may be molded, stamped or otherwise manufactured out of a substantially rigid metal or plastic, etc., and welded, glued, bolted or otherwise fixedly attached to the body member 61 a spaced distance from the second end 127 of the body member 61 to allow the sleeve 43 to fully extend when the first end 49 thereof is attached via the frame 53 to the frame track 141 and the second end 51 thereof is attached via the hook 129 to the second end 127 of the body member 61.

As stated hereinabove, the body member 62 preferably consist of an elongated, substantially rigid member such as a plastic plate or the like including a substantially flat first or inner face 95 and a substantially flat second or outer face 97. A third embodiment of the substantially rigid frame is shown in FIGS. 17, 18 and 21, especially designed and constructed for use with the body member 62, and identified by the numeral 153. The frame 153 is substantially similar to the frame 53 and is attached to a sleeve 43 about the entrance opening 47 in the sleeve 43. The frame 153 preferably has an opening 155 therethrough communicating with the entrance opening 47 in the sleeve 43 and the interior 45 of the sleeve 43 to allow the distal end 25 of the suction tube 21 to be inserted through the opening 155 in the frame 153, through the entrance opening 47 in the sleeve 43, and into the interior 45 of the sleeve 43. The frame 153 has a first or inner edge 156, a second or upper edge 157, a third or outer edge 158 and a fourth or lower edge 159. The frame 153 is preferably constructed of a material that is rigid, and that is also impermeable to viral and bacterial contamination. The frame 153 may be made of any impermeable, substantially rigid plastic, paper or the like in any manner now apparent to those skilled in the art such as, for example, by being extruded from a plastic material, etc., and glued to, or formed as an one-piece, integral unit with, the first end 49 of the sleeve 43, etc. However, unlike the frame 53, the inner edge 156 of the frame 153 is preferably attached to the body member 62 by way of a hinge member 161. The hinge member 161 may consist of a flexible tab or the like molded or otherwise attached to both the first edge 156 of the frame 153 and the body member 62 to provide a hinge to allow the frame 153 to be manually moved from a closed, stored position as shown in FIG. 17, to an opened, ready-for-use position as shown in FIGS. 18 and 21. Preferably, the body member 62, clamp 93, frame 153, and hinge member 161 are molded or otherwise formed out of a plastic material or the like as an integral, one-piece unit. Means, such as coacting tabs 163 and slots 165 are preferably provided to allow the frame 153 to be locked in the opened, ready-for-use position as will now be apparent to those skilled in the art. In this self-contained embodiment, the second end 51 of the sleeve 43 may be glued or otherwise permanently attached to the second end of the body member 62 rather than being removably attached thereto via a hook-and-aperture arrangement as shown with respect to the body member 61.

The oral suction device holder of the present invention may include a clamp 171 for allowing the flexible hose 17 of the oral suction device 15 to be clamped thereto when desired. The clamp 171 preferably consists of a typical spring-type pinch or squeeze clamp well known to those skilled in the art for being glued, bolted or otherwise securely attached to a respective body member 61, 62 in a position to allow the user of the oral suction device 15 to easily insert a portion of the flexible hose 17 therein when using the oral suction device holder of the present invention.

A second embodiment of the sleeve is shown in FIGS. 26–30, and identified by the numeral 181. The sleeve 181 is similar to the sleeve 43, and includes an external or main body or sleeve 182 having an interior 183, a mouth or entrance opening 185 communicating with the interior 183, a first or proximal end 187 adjacent the entrance opening 185, a second or distal end 189 opposite the entrance opening 185, and, perhaps, an aperture 191 through the second end 189. Reference should be made to the above description of the sleeve 43 for a more complete understanding of the structure and manufacture of the outer sleeve 182. In addition to the elements of the sleeve 43, the sleeve 181 includes an external pouch 193 preferably attached to the outer sleeve 182 for holding at least the distal end of an oral suction device such as the distal end 195 of a typical flexible catheter 197 or the like (see, in general, FIGS. 29 and 30). The external pouch 193 preferably has an opened top 199 through which at least the distal end of the oral suction device (e.g., the distal end 195 of the flexible catheter 197) can be inserted. The external pouch 193 may include means 201 for selectively closing the opened top thereof such as, for example, a typical ridge-and-groove "zipper" type seal or lock means found on many plastic bags and the like.

The outer sleeve 182 preferably has an internal pocket 203 to contain the external pouch 193 when the external pouch 193 is not needed. The outer sleeve 182 preferably has an opened slot or aperture 205 communicating with the internal pocket 203 and through which the external pouch 193 can extend as clearly shown in FIGS. 29 and 30. The outer sleeve 182 may include a tear strip 207 or the like whereby the slot 205 is normally closed and whereby the user of the sleeve 181 can easily open the slot 205 by tearing off or otherwise opening the strip 207, etc.

The outer sleeve 182, external pouch 193, internal pocket 203, and tear strip 207 are preferably constructed of a material that is flexible, and that is impermeable to viral and bacterial contamination, and may be made of any impermeable plastic, paper or rubber, etc. The outer sleeve 182 may be constructed as an elongated tube-like structure having one opened end and one closed end in any manner now apparent to those skilled in the art such as, for example, by being extruded from a plastic material, etc. The external pouch 193 may be constructed as an elongated bag-like structure having one opened end and one closed end in any manner now apparent to those skilled in the art such as, for example, by being extruded from a plastic material, etc., preferably with an upper edge thereof glued or otherwise fixedly attached to the internal pocket 203, etc. The opened slot 205 may be merely cut into one side of the outer sleeve 182 and the internal pocket 203 may be formed by gluing or otherwise attaching the edges of a generally rectangular shaped sheet of plastic material or the like to the internal wall of the outer sleeve 182 so that a pocket is formed around the slot 205 as will now be apparent to those skilled in the art. The tear strip 207 may consist of a generally rectangular shaped strip of plastic material or the like with the edges thereof lightly glued or with perforations formed therein in a manner to allow the tear strip 207 to be easily torn from the outer sleeve 182, leaving the slot 205 open to allow the user of the sleeve 181 to easily reach through the opened slot 205, grasp a portion of the external pouch 193, and pull the external pouch 193 from the internal pocket 203 as shown in FIGS. 29 and 30.

While the sleeve 181 is shown in FIGS. 26–30 in combination with a substantially rigid frame 53' as disclosed hereinabove relative to FIGS. 10 and 11, it should be understood that the sleeve 181 could be combined with other embodiments of the frame such as the frame 53 shown in FIGS. 1, 6, 8 and 9, or the frame 153 shown in FIGS. 17, 18 and 21, etc. Also, while the sleeve 181 is shown with an aperture 191 for use with a hook or hook-like member such as the hook-like member 129 of the body member 61 as shown generally in FIGS. 1 and 7–9, the sleeve 181 could be part of self-contained embodiment with the second end 189 thereof glued or otherwise permanently attached to the second end of a body member such as the body member 62 shown in FIGS. 17–20.

A third embodiment of the sleeve is shown in FIGS. 31–34, and identified by the numeral 211. The sleeve 211 is similar to the sleeve 43, and includes an external or main body or sleeve 212 having an interior 213, a mouth or entrance opening 215 communicating with the interior 213, a first or proximal end 217 adjacent the entrance opening 215, a second or distal end 219 opposite the entrance opening 215, and, perhaps, an aperture 221 through the second end 219. Reference should be made to the above description of the sleeve 43 for a more complete understanding of the structure and manufacture of the outer sleeve 212.

In addition to the elements of the sleeve 43, the sleeve 211 includes an internal bag 223 to hold at least the distal end of an oral suction device. As clearly shown in FIGS. 32 and 33, the internal bag 223 preferably is constructed as an elongated tube-like structure having an interior 225, a mouth or entrance opening 227 communicating with the interior 225, a first or proximal end 229 adjacent the entrance opening 227, and a second or distal end 231 opposite the entrance opening 227. The first end 229 of the internal bag 223 is fixedly attached to the inner wall of the interior 213 of the outer sleeve 212 by being glued or heat sealed thereto, or by being constructed integral therewith, etc., in a location so that the second end 231 of the internal bag 223 is positioned adjacent the second end 219 of the outer sleeve 212 as clearly shown in FIGS. 32 and 33. The midportion and the second end 231 of the internal bag 223 are free of the outer sleeve 212 so that the midportion and second end 231 of the internal bag 223 can be easily pulled away from the outer sleeve 212 as shown in FIG. 33. At least the distal or second end 231 of the internal bag 223 is flexible to selectively collapse around the distal end of an oral suction device, such as, for example, the distal end 25 of the suction tube 21 as clearly shown in FIG. 33. Preferably, the entire internal bag 223 is substantially more flexible than the outer sleeve 212 to more easily collapse around the distal end of the oral suction device. Thus, for example, the internal bag 223 can be merely constructed from a thinner plastic than the outer sleeve 212 whereby the outer sleeve 212 provides strength and the internal bag 223 provides adequate flexibility, etc., as will now be apparent to those skilled in the art.

Figure 34:
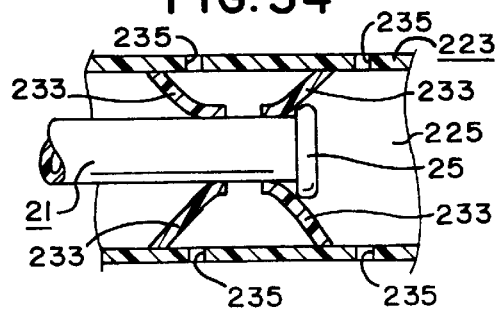
FIG. 34 is an enlarged view of a portion of FIG. 33 but showing the suction tube being removed from the internal bag and showing a plurality of internal flaps of the internal bag engaging the distal end of the suction tube.

The internal bag 223 preferably has a plurality of internal flaps 233 that engage the distal end of the oral suction device (e.g., the distal end 25 of the suction tube 21) when the oral suction device is removed from the internal bag 223 as shown in FIG. 34 to thereby clean or wipe the distal end of the oral suction device upon removal thereof from the sleeve 211 as will now be apparent to those skilled in the art. The internal bag 223 preferably has an aperture 235 therethrough beneath or adjacent each internal flap 233 to allow air to be pulled therethrough when the distal end of the oral suction device is inserted into the sleeve 43 and vacuum is supplied to the oral suction device, thereby pulling the distal end of each flap 233 away from the internal wall of the internal bag 223 and against the distal end of the oral suction device as will now be apparent to those skilled in the art. One or more vent apertures (not shown) may also be provided through the second end 219 of the outer sleeve 212.

The external sleeve 212 and internal bag 223 are preferably constructed of a material that is flexible, and that is impermeable to viral and bacterial contamination, and may be made of any impermeable plastic, paper or rubber, etc. The external sleeve 212 and main portion of the internal bag 223 may be constructed as elongated tube-like structures, each having one opened end and one closed end, in any manner now apparent to those skilled in the art such as, for example, by being extruded from a plastic material, etc. The flaps 233 may also be extruded or cut from a plastic material, etc., with one edge thereof glued or otherwise fixedly attached to the interior wall of the internal bag 223, etc. The apertures 235 may be merely cut into the internal bag 223 beneath or adjacent each flap 233.

Figure 31:
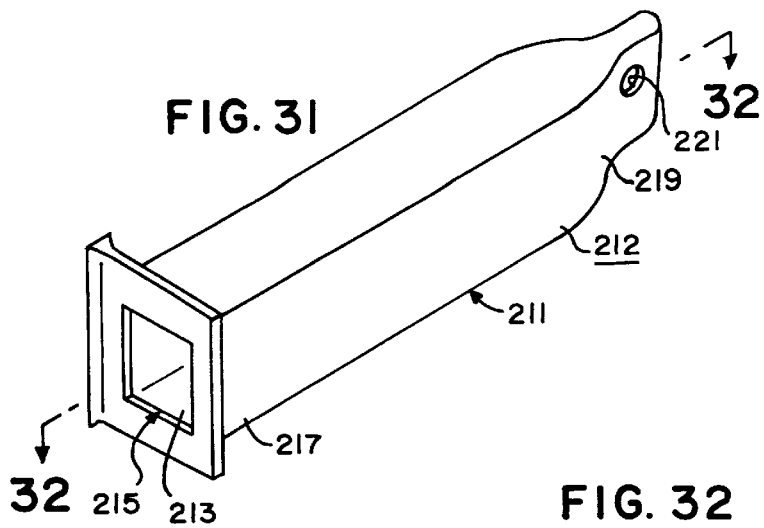
FIG. 31 is perspective view of a third embodiment of the sleeve of the oral suction device holder the present invention.
Figure 32:
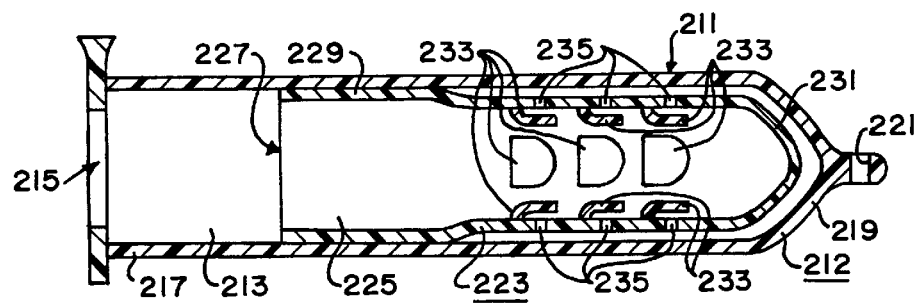
FIG. 32 is a sectional view substantially as taken on line 32—32 of FIG. 31 on a somewhat enlarged scale, showing an internal bag positioned within the sleeve.
Figure 33:
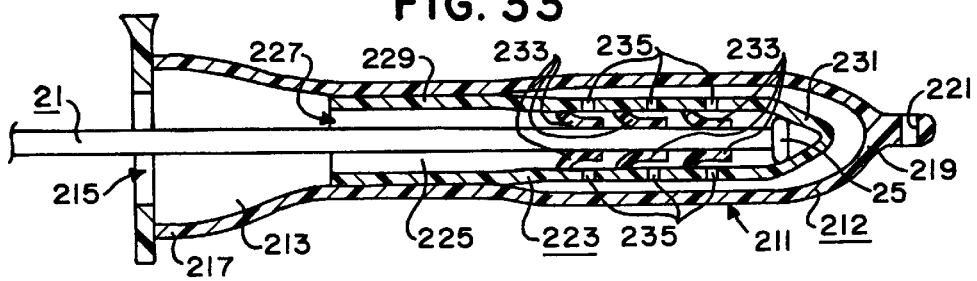
FIG. 33 is a sectional view similar to FIG. 32 but showing the distal end of a suction tube inserted into the internal bag with the internal bag collapsed about the distal end of the suction tube.

While the sleeve 211 is shown in FIGS. 31–33 in combination with a substantially rigid frame 53' as disclosed hereinabove relative to FIGS. 10 and 11, it should be understood that the sleeve 211 could be combined with other embodiments of the frame such as the frame 53 shown in FIGS. 1, 6, 8 and 9, or the frame 153 shown in FIGS. 17, 18 and 21, etc. Also, while the sleeve 211 is shown with an aperture 221 for use with a hook or hook-like member such as the hook-like member 129 of the body member 61 as shown generally in FIGS. 1 and 7–9, the sleeve 211 could be part of self-contained embodiment with the second end 219 thereof glued or otherwise permanently attached to the second end of a body member such as the body member 62 shown in FIGS. 17–20. Also, the sleeve 211 could include an external pouch and internal pocket such as the external pouch 193 and internal pocket 203 disclosed hereinabove relative to the sleeve 181.

Although the present invention has been described and illustrated with respect to preferred embodiments and preferred uses therefor, it is not to be so limited since modifications and changes can be made therein which are within the full intended scope of the invention.

I claim:

1. A holder for use with a support member and an oral suction device having a distal end for suctioning a patient's oral cavity; the holder comprising:

(a) a sleeve having an interior and an entrance opening communicating with the interior; the sleeve including an external pouch for holding at least the distal end of an oral suction device; and (b) a mount for mounting the sleeve to the support member so that the distal end of the oral suction device can be inserted into the sleeve after the sleeve is mounted to the support member.

2. The holder of claim 1 in which the external pouch has an opened top through which at least the distal end of the oral suction device can be inserted.

3. The holder of claim 2 in which the external pouch includes means for selectively closing the opened top thereof.

4. The holder of claim 2 in which the sleeve has an internal pocket to contain the external pouch when the external pouch is not needed.

5. The holder of claim 4 in which the sleeve has an aperture communicating with the internal pocket and through which the external pouch can extend.

6. The holder of claim 5 in which the sleeve includes a tear strip to selectively open the aperture communicating with the internal pocket of the sleeve.

7. A holder for use with a support member and an oral suction device having a distal end for suctioning a patient's oral cavity; the holder comprising:

(a) a sleeve having an interior and an entrance opening communicating with the interior; the sleeve including an internal bag to hold at least the distal end of an oral suction device; and (b) a mount for mounting the sleeve to the support member so that the distal end of the oral suction device can be inserted into the sleeve after the sleeve is mounted to the support member.

8. The holder of claim 7 in which at least the distal end of the internal bag is flexible to selectively collapse around the distal end of the oral suction device.

9. The holder of claim 7 in which the internal bag has a plurality of internal flaps that engage the distal end of the oral suction device when the oral suction device is removed from the internal bag.

10. The holder of claim 9 in which the internal bag has an aperture adjacent each internal flap.

* * * * *

UNITED STATES PATENT AND TRADEMARK OFFICE
CERTIFICATE OF CORRECTION

PATENT NO : 5,927,974
DATED : July 27, 1999
INVENTOR(S): Ronald H. Homra

It is certified that error appears in the above-identified patent and that said Letters Patent is hereby corrected as shown below:

On the title page, column one, item 76: please change "65 Stonewall Dr." to -65 Stonehaven Drive-.

Signed and Sealed this

Twenty-seventh Day of March, 2001

Attest:

NICHOLAS P. GODICI

Attesting Officer    Acting Director of the United States Patent and Trademark Office